United States Patent [19]

Takahashi et al.

[11] Patent Number: 4,946,865
[45] Date of Patent: Aug. 7, 1990

[54] DIPROPARGYLOXYBENZENE COMPOUNDS AND THEIR PRODUCTION

[75] Inventors: Junya Takahashi, Hyogo; Shigeko Nakamura, Otsu, both of Japan

[73] Assignee: Sumitomo Chemical Company, Limited, Osaka, Japan

[21] Appl. No.: 945,959

[22] Filed: Dec. 24, 1986

[30] Foreign Application Priority Data

| Dec. 27, 1985 | [JP] | Japan | 60-297281 |
| Dec. 27, 1985 | [JP] | Japan | 60-297282 |
| Dec. 28, 1985 | [JP] | Japan | 60-299208 |
| Dec. 28, 1985 | [JP] | Japan | 60-299209 |
| Mar. 4, 1986 | [JP] | Japan | 61-047008 |
| Mar. 4, 1986 | [JP] | Japan | 61-047011 |
| Mar. 5, 1986 | [JP] | Japan | 61-047820 |

[51] Int. Cl.$^5$ .................. A01N 37/34; A01N 31/14
[52] U.S. Cl. .................. 514/467; 514/520; 514/641; 514/701; 514/720; 558/391; 558/416; 558/422; 558/423; 560/64; 560/65; 562/473; 562/474; 564/176; 564/254; 564/256; 564/265; 568/442; 568/592; 568/631; 568/649; 568/651; 568/652; 568/654
[58] Field of Search ............. 568/649, 651, 652, 654, 568/592; 514/720, 467, 520, 523, 641, 701; 558/423; 549/453; 564/254, 256, 265

[56] References Cited

U.S. PATENT DOCUMENTS

| 3,288,834 | 11/1966 | Sterling et al. | 560/18 |
| 3,322,813 | 5/1967 | Seki et al. | 568/649 X |
| 3,338,950 | 8/1967 | Seki et al. | 568/649 X |
| 3,340,308 | 9/1967 | Sterling et al. | 568/640 |
| 3,362,871 | 1/1968 | Fellig et al. | 568/649 X |
| 3,816,541 | 6/1974 | Mihailovski et al. | 568/651 X |
| 3,840,604 | 10/1974 | Chodnekar et al. | 568/654 |
| 3,862,238 | 1/1975 | Mueller | 568/652 |
| 3,908,000 | 9/1975 | Chodnekar et al. | 514/720 |
| 4,235,932 | 11/1980 | Dorn et al. | 568/654 X |
| 4,356,329 | 10/1982 | Bettarni et al. | 568/649 X |

FOREIGN PATENT DOCUMENTS

A249567  5/1986  European Pat. Off. .
2156920  11/1971  Fed. Rep. of Germany .

Primary Examiner—Joseph Paul Brust
Attorney, Agent, or Firm—Birch, Stewart, Kolasch & Birch

[57] ABSTRACT

A compound of the formula:

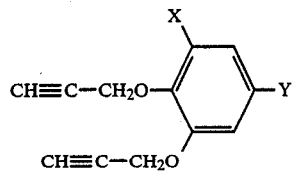

wherein X is a hydrogen atom, a halogen atom, a $C_1-C_3$ alkyl group or a $C_1-C_3$ alkoxy group and Y is a hydrogen atom, a halogen atom, a cyano group, a formyl group, an ethylene-dioxymethyl group, a hydroxyl group, a hydroxymethyl group or a group of either one of the formulas: $-CH=N-OR^1$, $-COOR^2$, $-CONH-R^2$ and $-CH(OR^3)_2$ in which $R^1$ is a hydrogen atom, a $C_1-C_3$ alkyl group, a $C_3-C_5$ alkenyl group, a $C_3-C_5$ alkynyl group, a halo($C_3-C_5$)alkynyl group or a $C_1-C_3$ alkyl group substituted with a phenyl group or a cyano group, $R^2$ is a hydrogen atom, a $C_1-C_3$ alkyl group, a $C_3-C_5$ alkenyl group or a $C_3-C_5$ alkynyl group and $R^3$ is a $C_1-C_3$ alkyl group, with the proviso that X and Y are not simultaneously hydrogen atoms, which is useful as a fungicidal agent against phytopathogenic fungi, particularly their strains resistant to benzimidazole or thiophanate fungicides and/or cyclic imide fungicides.

2 Claims, No Drawings

DIPROPARGYLOXYBENZENE COMPOUNDS AND THEIR PRODUCTION

This invention relates to dipropargyloxybenzene compounds and their production.

Benzimidazole and thiophanate fungicides such as Benomyl (methyl 1-(butylcarbamoyl)benzimidazol-2-ylcarbamate), Fubelidazol (2-(2-furyl)benzimidazole), Thiabendazole (2-(4-thiazolyl)benzimidazole), Carbendazim (methyl benzimidazol-2-ylcarbamate), Thiophanate-methyl (1,2-bis(3-methoxycarbonyl-2-thioureido)benzene), Thiophanate (1,2-bis(3-ethoxycarbonyl-2-thioureido)benzene), 2-(O,S-dimethylphosphorylamino)-1-(3'-methoxycarbonyl-2'-thioureido)benzene and 2-(O,O-dimethylthiophosphorylamino)-1-(3'-methoxycarbonyl-2'-thioureido)benzene are known to show an excellent fungicidal activity against various plant pathogenic fungi, and they have been widely used as agricultural fungicides since 1970. However, their continuous application over a long period of time provides phytopathogenic fungi with tolerance to them, whereby their plant disease-preventive effect is greatly lowered. Further, the fungi which gained tolerance to certain kinds of benzimidazole or thiophanate fungicides also show considerable tolerance to some other kinds of benzimidazole or thiophanate fungicides. Thus, they are apt to obtain cross-tolerance. Therefore, if any material decrease of their plant disease-preventive effect in certain fields is observed, their application to such fields has to be discontinued. But, it is often observed that the density of drug-resistant organisms is not decreased even long after the discontinuation of the application. Although other kinds of fungicides have to be employed in such cases, only few are so effective as benzimidazole or thiophanate fungicides in controlling various phytopathogenic fungi.

Cyclic imide fungicides such as Procymidone (3-(3',5'-dichlorophenyl)-1,2-dimethylcyclopropane-1,2-dicarboximide), Iprodione (3-(3',5'-dichlorophenyl)-1-isopropylcarbamoylimidazolidine-2,4-dione), Vinchlozolin (3-(3',5'-dichlorophenyl)-5-methyl-5-vinyloxazolidin-2,4-dione) and ethyl (RS)-3-(3',5'-dichlorophenyl)-5-methyl-2,4-dioxooxazolidine-5-carboxylate, which are effective against various plant diseases, particularly those caused by Botrytis cinerea, have the same defects as previously explained with respect to the benzimidazole or thiophanate fungicides.

As a result of the study seeking a new type of fungicides, it has now been found that dipropargyloxybenzene compounds of the formula:

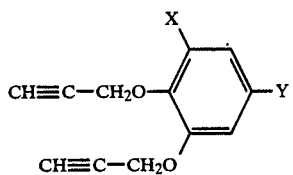

(I)

wherein X is a hydrogen atom, a halogen atom, a $C_1$–$C_3$ alkyl group or a $C_1$–$C_3$ alkoxy group and Y is a hydrogen atom, a halogen atom, a cyano group, a formyl group, an ethylenedioxymethyl group, a hydroxyl group, a hydroxymethyl group or a group of either one of the formulas: —CH=N—OR$^1$, —COOR$^2$, —CONH—R$^2$ or —CH(OR$^3$)$_2$, in which R$^1$ is a hydrogen atom, a $C_1$–$C_3$ alkyl group, a $C_3$–$C_5$ alkenyl group, a $C_3$–$C_5$ alkynyl group, a halo($C_3$–$C_5$)alkynyl group or a $C_1$–$C_3$ alkyl group substituted with a phenyl group or a cyano group, R$^2$ is a hydrogen atom, a $C_1$–$C_3$ alkyl group, a $C_3$–$C_5$ alkenyl group or a $C_3$–$C_5$ alkynyl group and R$^3$ is a $C_1$–$C_3$ alkyl group, with the proviso that X and Y are not simultaneously hydrogen atoms show an excellent fungicidal activity against plant pathogenic fungi which have developed resistance to benzimidazole, thiophanate and/or cyclic imide fungicides. It is notable that their fungicidal potency against the organisms tolerant to benzimidazole, thiophanate and/or cyclic imide fungicides (hereinafter referred to as "drug-resistant fungi" or "drug-resistant strains") is much higher than that against the organisms sensitive to benzimidazole, thiophanate and/or cyclic imide fungicides (hereinafter referred to as "drug-sensitive fungi" or "drug-sensitive strains").

The dipropargyloxybenzene compounds (I) are fungicidally effective against a wide scope of plant pathogenic fungi, of which examples are as follows: Podosphaera leucotricha, Venturia inaequalis, Mycosphaerella pomi, Marssonina mali and Sclerotinia mali of apple, Phyllactinia kakicola and Gloeosporium kaki of persimmon, Cladosporium carpophilum and Phomopsis sp of peach, Cercospora viticola, Uncinula necator, Elsinoe ampelina and Glomerella cingulata of grape, Cercospora beticola of sugarbeet, Cercospora arachidicola and Cercospora personata of peanut, Erysiphe graminis f. sp. hordei, Pseudocercosporella herpotrichoides and Fusarium nivale of barley, Erysiphe graminis f. sp. tritici of wheat, Sphaerotheca fuliginea and Cladosporium cucumerinum of cucumber, Cladosporium fulvum of tomato, Corynespora melongenae of eggplant, Sphaerotheca humuli, Fusarium oxysporum f. sp. fragariae of strawberry, Botrytis alli of onion, Cercospora apii of cerely, Phaeoisariopsis griseola of kidney bean, Erysiphe cichoracearum of tobacco, Diplocarpon rosae of rose, Elsinoe fawcetti, Penicillium italicum, Penicillium digitatum of orange, Botrytis cinerea of cucumber, eggplant, tomato, strawberry, pimiento, onion, lettuce, grape, orange, cyclamen, rose or hop, Sclerotinia sclerotiorum of cucumber, eggplant, pimiento, lettuce, celery, kidney bean, soybean, azuki bean, potato or sunflower, Sclerotinia cinerea of peach or cherry, Mycosphaerella melonis of cucumber or melon, etc. Namely, the dipropargyloxybenzene compounds (I) are highly effective in controlling the drug-resistant strains of said fungi. Besides, the dipropargyloxybenzene compounds (I) can also exert a significant antifungal activity against Pyricularia oryzae, Pseudoperonospora cubensis, Plasmopara, viticola, Phytophthora infestans, etc.

Advantageously, the dipropargyloxybenzene compounds (I) are low toxicity and have little detrimental actions on mammals, fishes and so on. Also, they may be applied to the agricultural field without causing any material toxicity to important crop plants.

From the viewpoint of exertion of fungicidal properties, notable are those of the formula:

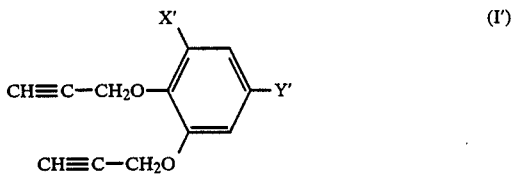

(I')

wherein X' is a halogen atom and Y' is a hydrogen atom, a halogen atom, a cyano group, a formyl group, an ethylenedioxymethyl group or a group of either one of the formulas: —CH=N—OR$^{1'}$,

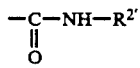

or —CH(OR$^{3'}$)$_2$ in which R$^{1'}$ is a hydrogen atom, a methyl group, an allyl group, a propargyl group, a cyanomethyl group or a benzyl group, R$^{2'}$ is an allyl group or a propargyl group and R$^{3'}$ is a methyl group. Particularly notable are those of the formula:

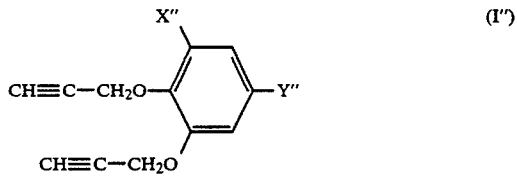

wherein X" is a chlorine atom or a bromine atom and Y" is a hydrogen atom, a chlorine atom, a bromine atom, a cyano group, a formyl group or a group of, either one of the formulas: —CH=N—OR$^{1''}$ or

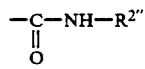

in which R$^{1''}$ is a hydrogen atom or a methyl group and R$^{2''}$ is an allyl group or a propargyl group.

The dipropargyloxybenzene compounds (I) can be prepared by various procedures, of which typical ones are shown below:

Procedure (a):
A compound of the formula:

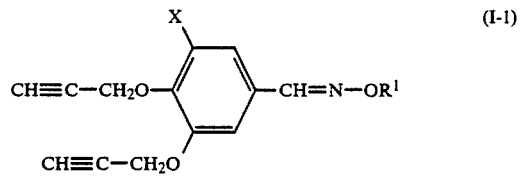

wherein X and R$^1$ are each as defined above is prepared by reacting a compound of the formula:

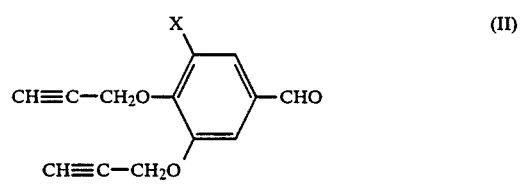

wherein X is as defined above with a compound of the formula:

$H_2N$—OR$^1$     (III)

wherein R$^1$ is as defined above.

The reaction is usually carried out in an inert solvent (e.g. N,N-dimethylformamide, methanol, ethanol, tetrahydrofuran, acetonitrile, chloroform, toluene, water, their mixtures) at a temperature from —60° C. to the boiling point of the solvent within about 12 hours.

Procedure (b):
A compound of the formula:

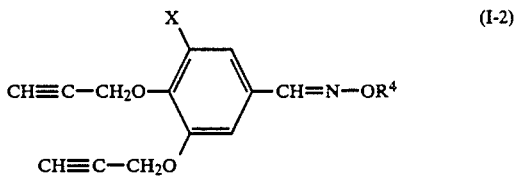

wherein X is as defined above and R$^4$ is a C$_1$-C$_3$ alkyl group, a C$_3$-C$_5$ alkenyl group, a C$_3$-C$_5$ alkynyl group, a halo(C$_3$-C$_5$)alkynyl group or a C$_1$-C$_3$ alkyl group substituted with a phenyl group or a cyano group is prepared by reacting a compound of the formula:

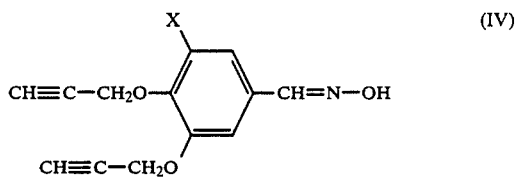

wherein X is as defined above with a compound of the formula:

R$^4$—Z     (V)

wherein R$^4$ is as defined above and Z is a leaving group (e.g. halogen, tosyloxy, mesyloxy) or a compound of the formula:

(R$^{4'}$O)$_2$SO$_2$     (VI)

wherein R$^{4'}$ is a C$_1$-C$_3$ alkyl group.

The reaction is usually carried out in an inert solvent (e.g. N,N-dimethylformamide, methanol, ethanol, tetrahydrofuran, acetonitrile, chloroform, toluene, water, their mixtures) in the presence of a base at a temperature from 0° to 200° C., preferably from room temperature to 90° C., within about 12 hours. Examples of the base are sodium hydride, triethylamine, pyridine, sodium hydroxide, potassium hydroxide, sodium carbonate, potassium carbonate, etc. A phase transfer catalyst (e.g. tetra-n-butylammonium bromide) may be used in the reaction, if desired.

Procedure (c):
A compound of the formula:

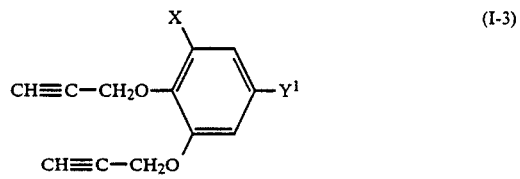

wherein X is as defined above and Y$^1$ is a hydrogen atom, a halogen atom, a cyano group or a hydroxyl group is prepared by diazotization of a compound of the formula:

$$\begin{array}{c}\text{CH}\equiv\text{C}-\text{CH}_2\text{O}\underset{\text{CH}\equiv\text{C}-\text{CH}_2\text{O}}{\overset{\text{X}}{\diagdown\diagup}}\text{NH}_2\end{array}\quad\text{(VII)}$$

wherein X is as defined above, followed by decomposition of the resulting diazonium salt.

In the diazotization, the compound (VII) may be allowed to react with a nitrite such as an alkali metal nitrite (e.g. sodium nitrite, potassium nitrite), an alkaline earth metal nitrite (e.g. barium nitrite) or an alkyl nitrite (e.g. methyl nitrite). Further, the reaction is carried out in the absence or presence of an inert solvent (e.g. water, dioxane, acetone, their mixtures) in the existence of an acid (e.g. hydrochloric acid, sulfuric acid, hydrobromic acid, formic acid, acetic acid).

The decomposition proceeds in the presence of an alcohol (e.g. methanol, ethanol) or hydrophosphorus acid at a temperature of room temperature to 150° C. with about 12 hours to give the compound (I-3) wherein $Y^1$ is hydrogen. When a copper halide (e.g. copper chloride, copper bromide) is used in place of an alcohol or hydrophosphorus acid, there is obtained the compound (I-3) wherein $Y^1$ is halogen. Likewise, the use of copper cyanide gives the compound (I-3) wherein $Y^1$ is cyano, and the use of sulfuric acid gives the compound (I-3) wherein $Y^1$ is hydroxyl.

The compound (VII) is obtainable according to the procedure as described in Japanese Patent Publn. (unexamined) No. 83148/1986.

Procedure (d):

A compound of the formula:

$$\begin{array}{c}\text{CH}\equiv\text{C}-\text{CH}_2\text{O}\underset{\text{CH}\equiv\text{C}-\text{CH}_2\text{O}}{\overset{\text{X}}{\diagdown\diagup}}\text{Y}^2\end{array}\quad\text{(I-4)}$$

wherein X is as defined above and $Y^2$ is a hydrogen atom, a halogen atom, a cyano group, a formyl group, an ethylenedioxymethyl group, a hydroxymethyl group or a group of either one of the formulas: —CH=N—OR$^1$, —COOR$^5$, —CONH—R$^2$ or —CH(OR$^3$)$_2$ in which R$^1$, R$^2$ and R$^3$ are each as defined above and R$^5$ is a C$_1$–C$_3$ alkyl group, a C$_3$–C$_5$ alkenyl group or a C$_3$–C$_5$ alkynyl group is prepared by reacting a compound of the formula:

$$\begin{array}{c}\text{HO}\underset{\text{HO}}{\overset{\text{X}}{\diagdown\diagup}}\text{Y}^2\end{array}\quad\text{(VIII)}$$

wherein X and $Y^2$ are each as defined above with propargyl halide.

The reaction is usually carried out in an inert solvent (e.g. N,N-dimethylformamide, tetrahydrofuran, acetonitrile, chloroform, toluene, water, their mixtures) in the presence of a base (e.g. sodium hydride, triethylamine, pyridine, sodium hydroxide, potassium hydroxide, sodium carbonate, potassium carbonate) at a temperature from 0° to 120° C., preferably from room temperature to 90° C., within about 12 hours.

The compound (VIII) can be prepared according to the method as described in J. Chem. Soc., Perkin 1, 1015 (1973).

Procedure (e):

A compound of the formula:

$$\begin{array}{c}\text{CH}\equiv\text{C}-\text{CH}_2\text{O}\underset{\text{CH}\equiv\text{C}-\text{CH}_2\text{O}}{\overset{\text{X}}{\diagdown\diagup}}\text{Y}^3\end{array}\quad\text{(I-5)}$$

wherein X is as defined above and $Y^3$ is a group of either one of the formulas: —COOR$^5$ or —CONH—R$^2$ in which R$^2$ is as defined above and R$^5$ is a C$_1$–C$_3$ alkyl group, a C$_3$–C$_5$ alkenyl group or a C$_3$–C$_5$ alkynyl group is prepared by reacting a compound of the formula:

$$\begin{array}{c}\text{CH}\equiv\text{C}-\text{CH}_2\text{O}\underset{\text{CH}\equiv\text{C}-\text{CH}_2\text{O}}{\overset{\text{X}}{\diagdown\diagup}}\underset{\text{O}}{\overset{\phantom{O}}{\text{C}-\text{Z}'}}\end{array}\quad\text{(IX)}$$

wherein X is as defined above and Z' is a halogen atom with a compound of the formula:

$$R^5-\text{OH}\quad\text{(X)}$$

or $$R^2-\text{NH}_2\quad\text{(XI)}$$

wherein R$^5$ and R$^2$ are each as defined above.

The reaction is usually carried out in the absence or presence of an inert solvent (e.g. N,N-dimethylformamide, tetrahydrofuran, acetonitrile, chloroform, toluene, water, their mixtures) at a temperature from −10° C. to the boiling point of the reaction mixture within about 12 hours. A base (e.g. N,N-diethylaniline, triethylamine, pyridine, sodium hydroxide, potassium hydroxide, sodium carbonate, potassium carbonate) may be present in the reaction system.

The starting compound (IX) is obtainable by reacting a compound of the formula:

$$\begin{array}{c}\text{CH}\equiv\text{C}-\text{CH}_2\text{O}\underset{\text{CH}\equiv\text{C}-\text{CH}_2\text{O}}{\overset{\text{X}}{\diagdown\diagup}}\text{COOH}\end{array}\quad\text{(XII)}$$

wherein X is as defined above with a halogenating agent (e.g. thionyl chloride, thionyl bromide, phosgene) in the absence or presence of an inert solvent (e.g. benzene, toluene, hexane, tetrahydrofuran, their mixtures) at a temperature from room temperature to the boiling point of the reaction mixture within about 12 hours.

A typical example or preparation of the compound (IX) is illustratively shown in the following example.

Reference Example

A mixture of 3-chloro-4,5-dipropargyloxybenzoic acid (10.7 g) and thionyl chloride (30 ml) was stirred under reflux for 1 hour. After cooling, the reaction mixture was evaporated under reduced pressure to give 3-chloro-4,5-dipropargyloxybenzoyl chloride in a quantitative yield.

IR (Nujol): 3275, 2100, 1740, 1140, 820 cm$^{-1}$.

NMR δ TMS (CDCl$_3$): 7.85 (d, 1H), 7.65 (d, 1H), 4.90 (d, 2H), 4,80 (d, 2H), 2.40–2.70 (2H).

Procedure (f):

A compound of the formula:

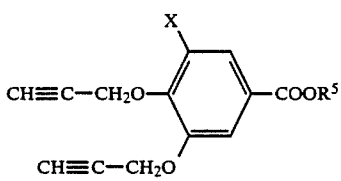
(I-6)

wherein X and R$^5$ are each as defined above is prepared by reacting the compound (XII) with a compound of the formula:

$$R^5-Z''$$ (V')

wherein R$^5$ is as defined above and Z'' is a leaving group (e.g. halogen, mesyloxy, tosyloxy).

The reaction is usually carried out in an inert solvent (e.g. N,N-dimethylformamide, tetrahydrofuran, acetonitrile, chloroform, toluene, water, their mixtures) in the presence of a base (e.g. sodium hydride, triethylamine, pyridine, sodium hydroxide, potassium hydroxide, sodium carbonate, potassium carbonate) at a temperature from 0° to 120° C., preferably from room temperature to 90° C., within about 12 hours.

Procedure (g):

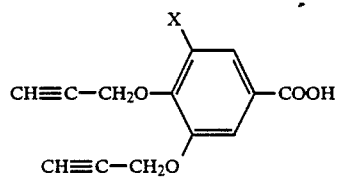
(I-7)

wherein X is as defined above is prepared by oxidation of the compound (II).

Examples of the oxidizing agent are Jones reagent, manganese dioxide, potassium permanganate, pyridinium chlorochromate, etc. The reaction is usually carried out in an inert solvent (e.g. water, acetone, benzene, toluene, hexane, dichloromethane, carbon tetrachloride, their mixture) at a temperature of 0° to 100° C. within about 12 hours.

Procedure (h):

A compound of the formula:

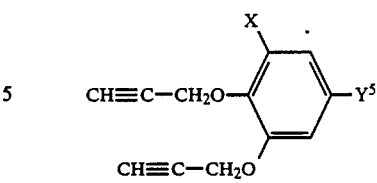
(I-8)

wherein X is as defined above and Y$^5$ is an ethylenedioxymethyl group or a group of the formula: —CH(OR$^3$)$_2$ in which R$^3$ is as defined above is prepared by reacting the compound (II) with ethylene glycol or a compound of either one of the formulas: CH(OR$^3$)$_3$ or R$^3$OH in which R$^3$ is as defined above.

The reaction is ordinarily carried out in the absence or presence of an inert solvent (e.g. methanol, ethanol, benzene, toluene, xylene, chloroform, carbon tetrachloride, their mixtures) at a temperature from 0° C. to the boiling point of the reaction mixture for a period of about 15 minutes to 12 hours.

Procedure (i):

A compound of the formula:

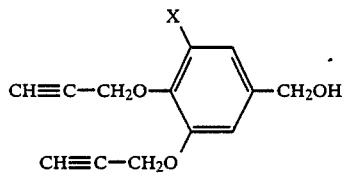
(I-9)

wherein X is as defined above is prepared by reducing the compound (II).

Examples of the reducing agent are sodium borohydride, lithium aluminium hydride, aluminium ethoxide, aluminium isopropoxide, etc. The reduction is performed in the presence of an inert solvent (e.g. water, methanol, ethanol, benzene, toluene, hexane, ethyl acetate, dioxane, tetrahydrofuran) at a temperature from −10° to 100° C. within about 12 hours.

Still, the compound (I-1) can have syn- and anti-isomers and represent such syn- or anti-isomer, or their mixture, inclusively.

Some typical examples for preparation of the compound (I) are illustratively shown in the following examples.

EXAMPLE 1

Preparation of 3-chloro-4,5-dipropargyloxybenzaldehyde oxime O-methyl ether according to Procedure (a)

Sodium hydride (0.17 g; 60% dispersion in mineral oil) was dissolved in ethanol (50 ml). To this mixture, O-methylhydroxylamine hydrochloride (0.34 g) was added. After stirring at room temperature for 30 minutes, 3-chloro-4,5-dipropargyloxybenzaldehyde (1.00 g) was added thereto, and the resultant mixture was stirred under reflux for 30 minutes. The reaction mixture was poured into ice-water and extracted with ethyl acetate. The extract was washed with water, dried over magnesium sulfate and concentrated under reduced pressure. The residue was washed with hexane to give 3-chloro-4,5-dipropargyloxybenzaldehyde oxime O-methyl ether (0.63 g).

NMR δ TMS (CDCl$_3$): 7.88 (s, 1H), 7.18 (s, 2H), 4.70–4.80 (4H), 3.94 (s, 3H), 2.40–2.60 (2H).

EXAMPLE 2

Preparation of
3-chloro-4,5-dipropargyloxybenzaldehyde oxime
O-allyl ether according to Procedure (b)

3-Chloro-4,5-dipropargyloxybenzaldehyde oxime (0.45 g), potassium hydroxide (0.50 g), allyl bromide (0.40 g) and tetra-n-butylammonium bromide (0.50 g) were dissolved in tetrahydrofuran (20 ml), and the resultant solution was stirred at room temperature for 2 hours. The reaction mixture was poured into ice-water and extracted with ethyl acetate. The extract was washed with water, dried over magnesium sulfate and concentrated under reduced pressure. The residue was subjected to silica gel chromatography using toluene as an eluent to give 3-chloro-4,5-dipropargyloxybenzaldehyde oxime O-allyl ether (0.43 g). m.p. 51°–53° C.

EXAMPLE 3

Preparation of 1,3-dichloro-4,5-dipropargyloxybenzene according to Procedure (c)

Sodium nitrite (1.33 g) was added to a solution of 3-chloro-4,5-dipropargyloxyaniline (4.47 g) in acetic acid (30 ml) and 35% hydrochloric acid (4 ml) at 0° C., followed by stirring at the same temperature for 1 hour. The resultant solution was poured into 35% hydrochloric acid (20 ml) containing copper chloride (2.35 g) at room temperature, and stirring was continued at 60° C. for 30 minutes. The reaction mixture was poured into ice-water and extracted with ethyl acetate. The extract was washed with aqueous sodium carbonate solution, dried over magnesium sulfate and concentrated under reduced pressure. The residue was subjected to silica gel chromatography using toluene as an eluent to give 1,3-dichloro-4,5-dipropargyloxybenzene (3.60 g) as white crystals. m.p. 61°–63° C.

EXAMPLE 4

Preparation of
3-chloro-4,5-dipropargyloxybenzaldehyde according to Procedure (d)

Sodium hydride (2.69 g; 60% dispersion in mineral oil) was added to dimethylformamide (500 ml). To the mixture was added a solution of 3-chloro-4,5-dihydroxybenzaldehyde (11.6 g) in dimethylformamide (100 ml) at a temperature of 0° to 5° C., followed by stirring at room temperature for 1 hour. Propargyl bromide (8.00 g) was added thereto. The resultant mixture was heated at 90° C. for 5 minutes and cooled to 0° C., and sodium hydride (2.69 g) was added thereto. After the forming ceased, propargyl bromide (8.00 g) was added to the reaction mixture. The resultant mixture was heated at 90° C. for 5 minutes, poured into ice-water and extracted with ethyl acetate. The extract was washed with aqueous potassium carbonate solution and water, dried over magnesium sulfate and concentrated under reduced pressure. The residue was subjected to alumina chromatography using toluene as an eluent to give 3-chloro-4,5-dipropargyloxybenzaldehyde (5.46 g). m.p. 64°–65° C.

EXAMPLE 5

Preparation of 3-chloro-4,5-dipropargyloxybenzamide according to Procedure (e)

A solution of 3-choro-4,5-dipropargyloxybenzoyl chloride (1.00 g) in 30% ammonia water (20 ml) and toluene (10 ml) was stirred under reflux for 10 minutes, poured into ice-water and extracted with ethyl acetate. The extract was washed with water, dried over magnesium sulfate and concentrated under reduced pressure to give a residue. The residue was further washed with hexane to give 3-chloro-4,5-dipropargyloxybenzamide (0.88 g). m.p. 122°–125° C.

EXAMPLE 6

Preparation of propargyl
3-chloro-4,5-dipropargyloxybenzoate according to Procedure (f)

Sodium hydride (0.23 g; 60% dispersion in mineral oil) was added to a solution of 3-chloro-4,5-dipropargyloxybenzoic acid (1.50 g) in N,N-dimethylformamide (50 ml) at 0° C., followed by stirring at room temperature for 1 hour. Propargyl bromide (0.80 g) was added thereto, and the resultant mixture was stirred at 90° C. for 5 minutes, poured into ice-water and extracted with ethyl acetate. The extract was washed with an aqueous potassium carbonate solution, dried over magnesium sulfate and concentrated under reduced pressure. The residue was subjected to silica gel chromatography using toluene as an eluent to give propargyl 3-chloro-4,5-dipropargyloxybenzoate (1.03 g). m.p. 98°–99° C.

EXAMPLE 7

Preparation of 3-chloro-4,5-dipropargyloxybenzoic acid according to Procedure (g)

Jones reagent (e.g. an aqueous sulfuric acid solution of chromium trioxide) was added to a solution of 3-chloro-4,5-dipropargyloxybenzaldehyde (18.0 g) in acetone (100 ml) under stirring at a temperature below 20° C. The addition was stopped when the reaction mixture became red, and stirring was continued at 20° C. for 1 hour. The reaction mixture was poured into ice-water containing ethanol (100 ml) and extracted with ethyl acetate. The extract was washed with water, dried over magnesium sulfate and concentrated under reduced pressure. The residue was washed with hexane to give 3-chloro-4,5-dipropargyloxybenzoic acid (16.2 g). m.p. 158°–159° C.

EXAMPLE 8

Preparation of
3-chloro-4,5-diproprgyloxybenzaldehyde dimethyl acetal according to Procedure (h)

A solution of 3-chloro-4,5-dipropargyloxybenzaldehyde (1.0 g), trimethyl orthoformate (4.0 g) and ammonium chloride (0.05 g) in methanol (20 ml) was stirred under reflux for 3 hours, and the resultant solution was poured into ice-water and extracted with ethyl acetate. The extract was washed with water, dried over magnesium sulfate and concentrated under reduced pressure. The residue was subjected to alumina chromatography using toluene as an eluent to give 3-chloro-4,5-dipropargyloxybenzaldehyde dimetylacetal (0.94 g). $n_D^{21.0}$ 1.5344.

EXAMPLE 9

Preparation of
3-chloro-4,5-dipropargyloxybenzylalcohol according to Procedure (i)

3-Chloro-4,5-dipropargyloxybenzaldehyde (14.7 g) was added to a solution of sodium borohydride (3.6 g) in ethanol (150 ml) at a temperature below 30° C. After stirring at room temperature for 2 hours, the resultant mixture was poured into dilute hydrochloric acid under cooling and extracted with ethyl acetate. The extract was washed with water, dried over magnesium sulfate and concentrated under reduced pressure to give 3-chloro-4,5-dipropargyloxybenzyl alcohol (15.60 g). $n_D^{17.0}$ 1.5713.

In the same manner as above, the dipropargyloxybenzene compounds (I) of the invention as shown in Table 1 can be prepared.

TABLE 1

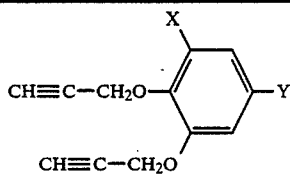
(I)

| Compound No. | X | Y | Physical constant |
|---|---|---|---|
| 1 | Cl | —CH=N—OH | NMR δ (TMS) (DMSO-d$_6$): 8.08 (s, 1H), 7.38 (d, 1H), 7.30 (d, 1H), 4.90 (d, 2H), 4.78 (d, 2H), 3.30–3.70 (3H) |
| 2 | Cl | —CH=N—OCH$_3$ | NMR δ (TMS) (CDCl$_3$): 7.88 (s, 1H), 7.18 (s, 2H), 4.70–4.80 (4H), 3.94 (s, 3H), 2.40–2.60 (2H) |
| 3 | Br | —CH=N—OH | m.p. 105–108° C. |
| 4 | Br | —CH=N—OCH$_3$ | m.p. 105–106° C. |
| 5 | Cl | —CH=N—OCH$_2$CH=CH$_2$ | m.p. 51–53° C. |
| 6 | Cl | —CH=N—OCH$_2$C≡CH | m.p. 82–83.5° C. |
| 7 | Cl | —CH=N—OCH$_2$CN | m.p. 77–78° C. |
| 8 | Cl | —CH=N—OCH$_2$C$_6$H$_5$ | $n_D^{17.0}$ 1.5890 |
| 9 | Cl | H | $n_D^{20.0}$ 1.5525 |
| 10 | Cl | Cl | m.p. 61–63° C. |
| 11 | Cl | CN | NMR δ TMS (CDCl$_3$): 7.35 (d, 1H), 7.25 (d, 1H), 4.75 (d, 2H), 4.70 (d, 2H), 2.48 (t, 1H), 2.38 (t, 1H) |
| 12 | Cl | OH | $n_D^{22.0}$ 1.5580 |
| 13 | Br | CN | m.p. 115–116° C. |
| 14 | Cl | Br | NMR δ TMS (CDCl$_3$): 7.18 (d, 1H), 7.05 (d, 1H), 4.70 (d, 4H), 2.55 (m, 2H) |
| 15 | Cl | —COOH | m.p. 158–159° C. |
| 16 | Cl | —COOCH$_3$ | m.p. 70–72° C. |
| 17 | Cl | —COOCH$_2$CH=CH$_2$ | NMR δ TMS (CDCl$_3$): 7.70 (d, 1H), 7.55 (d, 1H), 5.00–6.50 (3H), 4.65–4.90 (6H), 2.40–2.60 (2H) |
| 18 | Cl | —COOCH$_2$C≡CH | m.p. 98–99° C. |
| 19 | Cl | —COOC$_2$H$_5$ | m.p. 82–83° C. |
| 20 | Br | —COOH | m.p. 169–170° C. |
| 21 | Cl | —CHO | m.p. 64–65° C. |
| 22 | Cl | —CH(OCH$_3$)$_2$ | $n_D^{21.0}$ 1.5344 |
| 23 | Cl | —CH(O—CH$_2$)(O—CH$_2$) | m.p. 46–51° C. |

TABLE 1-continued $$\text{(I)}$$

Structure: benzene ring with X at one position, Y at another, and two CH≡C—CH₂O— groups.

| Compound No. | X | Y | Physical constant |
|---|---|---|---|
| 24 | Br | —CHO | m.p. 78–79° C. |
| 25 | Cl | —CH₂OH | $n_D^{17.0}$ 1.5713 |
| 26 | Cl | —C(=O)—NH₂ | m.p. 122–125° C. |
| 27 | Cl | —C(=O)—NH—CH₃ | m.p. 130–132° C. |
| 28 | Cl | —C(=O)—N(H)(CH₂CH=CH₂) | m.p. 65.5–66.5° C. |
| 29 | Cl | —C(=O)—N(H)(CH₂C≡CH) | m.p. 103–105° C. |
| 30 | Cl | F | $n_D^{23.0}$ 1.5354 |
| 31 | Cl | I | $n_D^{15.5}$ 1.6355 |
| 32 | CH₃ | Cl | m.p. 56–57.5° C. |
| 33 | —OCH₃ | I | $n_D^{18.0}$ 1.6549 |
| 34 | —OCH₃ | Cl | $n_D^{18.5}$ 1.5562 |
| 35 | Cl | —CH=N—O—CH₂C≡C—I | NMR δ TMS (CDCl₃): 8.00 (s, 1H), 7.22 (s, 2H), 4.80 (s, 6H), 2.50 (broad, 2H), |
| 36 | H | Cl | NMR δ TMS (CDCl₃): 6.88–6.98 (3H), 4.60–4.80 (4H), 2.45–2.75 (2H) |

In the practical usage of the dipropargyloxybenzene compounds (I) as fungicides, they may be applied as such or in a formulation form such as dusts, wettable powders, oil sprays, emulsifiable concentrates, tablets, granules, fine granules, aerosols or flowables. Such preparation form can be formulated in a conventional manner by mixing at least one of the dipropargylbenzene compounds (I) with an appropriate solid or liquid carriers(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are botanical materials (e.g. flour, tobacco stalk powder, soybean powder, walnut-shell powder, vegetable powder, saw dust, bran, bark powder, cellulose powder, vegetable extract residue), fibrous materials (e.g. paper, corrugated cardboard, old rags), synthetic plastic powders, clays (e.g. kaolin, bentonite, fuller's earth), talcs, other inorganic materials (e.g. pyrophyllite, sericite, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methylethylketone), ethers (e.g. diethyl ether, dioxane, cellosolve, tetrahydrofuran), aromatic hydrocarbons (e.g. benzene, toluene, xylene, methyl naphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, carbon tetrachloride), etc.

Examples of the surfactants are alkyl sulfuric esters, alkyl sulfonates, alkylaryl sulfonates, polyethylene glycol ethers, polyhydric alcohol esters, etc. Examples of the adherents and dispersants may include casein, gelatin, starch powder, carboxymethyl cellulose, gum arabic, alginic acid, lignin, bentonite, molasses, polyvinyl alcohol, pine oil and agar. As the stabilizers, there may be used PAP (isopropyl acid phosphate mixture), tricresyl phosphate (TCP), tolu oil, epoxydized oil, various surfactants, various fatty acids and their esters, etc.

The foregoing formulation generally contain at least one of the dipropargyloxybenzene compounds (I) in a concentration of about 1 to 95% by weight, preferably of 2.0 to 80% by weight. By using the formulations, the dipropargyloxybenzene compounds (I) are generally applied in such amounts as 2 to 100 g per 10 are.

When only the drug-resistant strains of phytopathogenic fungi are present, the dipropargyloxybenzene compounds (I) may be used alone. However, when the drug-sensitive strains are present together with the drug-resistant strains, their alternate use with benzimidazole, thiophanate and/or cyclic imide fungicides or their combined use with benzimidazole, thiophanate and/or cyclic imide fungicides is favorable. In such alternate or combined use, each active ingredient may be employed as such or in conventional agricultural formulation forms. In case of the combined use, the weight proportion of the dipropargyloxybenzene compound (I) and the benzimidazole, thiophanate and/or cyclic imide fungicide may be from about 1:0.1 to 1:10.0.

Typical examples of the benzimidazole, thiophanate and cyclic imide fungicides which are commercially available are shown in Table 2.

TABLE 2

| Compound | Structure | Name |
|---|---|---|
| A | 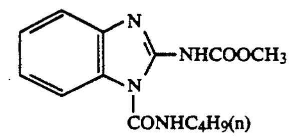 | Methyl 1-(butylcarbamoyl)benzimidazol-2-ylcarbamate |
| B | 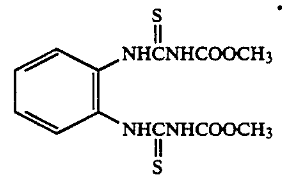 | 1,2-Bis(3-methoxycarbonyl-2-thioureido)benzene |
| C | 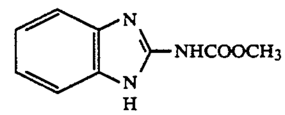 | Methyl benzimidazol-2-ylcarbamate |
| D | 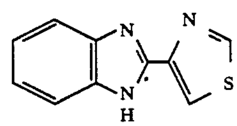 | 2-(4-Thiazolyl)benzimidazole |
| E | 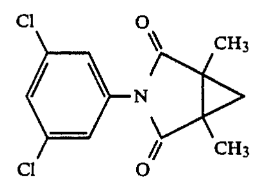 | N-(3',5'-Dichlorophenyl)-1,2-dimethylcyclopropane-1,2-dicarboximide |
| F | 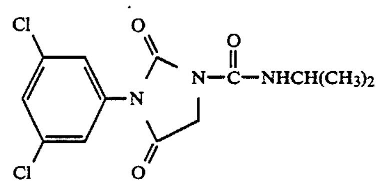 | 3-(3',5'-Dichlorophenyl)-1-isopropylcarbamoylimidazolidin-2,4-dione |
| G | 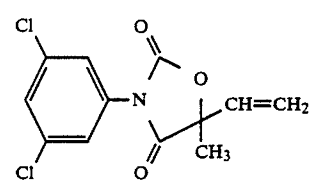 | 3-(3',5'-Dichlorophenyl)-5-methyl-5-vinyloxazolidin-2,4-dione |
| H | 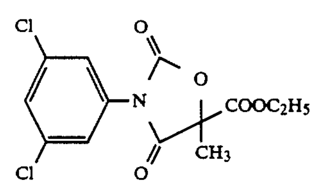 | Ethyl (RS)-3-(3',5'-dichlorophenyl)-5-methyl-2,4-dioxo-oxazolidine-5-carboxylate |

Besides, the dipropargyloxybenzene compounds (I) may be also used in admixture with other fungicides, herbicides, insecticides, miticides, fertilizers, etc.

When the dipropargyloxybenzene compounds (I) are used as fungicides, they may be applied in such amounts as 2 to 100 grams per 10 are. However, this amount may vary depending upon formulation forms, application times, application methods, application sites, diseases, crops and so on, and therefore, they are not limited to said particular amounts.

Some practical embodiments of the fungicidal composition according to the invention are illustratively shown in the following Examples wherein % and part(s) are by weight.

FORMULATION EXAMPLE 1

Two parts of each of Compound Nos. 1 to 36, 88 parts of kaolin clay and 10 parts of talc are thoroughly pulverized and mixed together to obtain a dust formulation containing 2% of the active ingredient.

FORMULATION EXAMPLE 2

Ten parts of each of Compound Nos. 1 to 36, 1 part of polyoxyethylene styrylphenyl ether as an emulsifier and 89 parts of water are mixed together to obtain an emulsifiable concentrate formulation containing 10% of the active ingredient.

FORMULATION EXAMPLE 3

Eighty parts of each of Compound Nos. 1 to 36, 10 parts of cyclohexanone and 10 parts of polyoxyethylene alkylaryl ether as an emulsifier are mixed together to obtain an emulsifiable concentrate formulation containing 80 of the active ingredient.

FORMULATION EXAMPLE 4

Two parts of each of Compound Nos. 1 to 36, 88 parts of clay and 10 parts of talc are thoroughly pulverized and mixed together to obtain a dust formulation containing 2 of the active ingredient.

FORMULATION EXAMPLE 5

One part of each of Compound Nos. 1 to 36, 1 part of Compound A, 88 parts of clay and 10 parts of talc are thoroughly pulverized and mixed together to obtain a dust formulation containing 2 parts of the active ingredient.

FORMULATION EXAMPLE 6

Twenty parts of each of Compound Nos. 1 to 36, 10 parts of Compound F, 45 parts of diatomaceous earth, 20 parts of white carbon, 3 parts of sodium laurylsulfate as a wetting agent and 2 parts of calcium ligninsulfonate as a dispersing agent are mixed while being powdered to obtain a wettable powder composition containing 30% of the active ingredient.

FORMULATION EXAMPLE 7

Ten parts of each of Compound Nos. 1 to 36, 40 parts of Compound B, 45 parts of diatomaceous earth, 2.5 parts of calcium alkylbenzenesulfonate as a wetting agent and 2.5 parts of calcium ligninsulfonate as a dispersing agent are mixed while being powdered to obtain a wettable powder composition containing 50% of the active ingredient.

FORMULATION EXAMPLE 8

Five parts of each of Compound Nos. 1 to 36, 5 parts of Compound C, 80 parts of cyclohexanone and 10 parts of polyoxyethylene alkylaryl ether as an emulsifier are mixed together to obtain an emulsifiable concentrate formulation containing 10% of the active ingredient.

Typical test data indicating the excellent fungicidal activity of the dipropargyloxybenzene compounds (I) are shown below.

EXPERIMENT 1

Preventive effect on gray mold of cucumber (*Botrytis cinerea*)

A plastic pot of 90 ml volume was filled with sandy soil, and seeds of cucumber (var: Sagami-hanjiro) were sowed therein. Cultivation was carried out in a greenhouse for 8 days to obtain cucumber seedlings expanding cotyledons. Onto the resulting seedlings, the test compound formulated in emulsifiable concentrate or wettable powder and diluted with water was sprayed at a rate of 30 ml per pot. After air-drying, the seedlings were inoculated with mycelial disks (5 mm in diameter) of the drug-resistant or drug-sensitive strain of *Botrytis cinerea* by putting them on the leaf surfaces. After the plants were infected by incubating under high humidity at 20° C. for 3 days, the rates of disease severity were observed. The degree of damage was determined in the following manner, and the results are shown in Table 3.

The leaves examined were measured for a percentage of infected area and classified into the corresponding disease indices, 0, 0.5, 1, 2, 4:

| Disease index | Percentage of infected area |
| --- | --- |
| 0 | No infection |
| 0.5 | Infected area of less than 5% |
| 1 | Infected area of not less than 5% but less than 20% |
| 2 | Infected area of not less than 20% but less than 50% |
| 4 | Infected area of not less than 50% |

The disease severity was calculated according to the following equation:

$$\text{Disease severity (\%)} = \frac{\Sigma\{(\text{Disease index}) \times (\text{Number of leaves})\}}{4 \times (\text{Total number of leaves examined})} \times 100$$

The prevention value was calculated according to the following equation:

$$\text{Prevention value (\%)} = 100 - \frac{(\text{Disease severity in treated plot})}{(\text{Disease severity in untreated plot})} \times 100$$

TABLE 3

| Compound No. | Concentration of active ingredient (ppm) | Prevention value when inoculated with drug-resistant strain (%) | Prevention value when inoculated with drug-sensitive strain (%) |
| --- | --- | --- | --- |
| 1 | 200 | 100 | 0 |
| 2 | 200 | 100 | 0 |
| 3 | 200 | 75 | 0 |
| 4 | 200 | 100 | 0 |
| 5 | 200 | 97 | 0 |
| 6 | 200 | 100 | 0 |
| 7 | 200 | 100 | 0 |
| 8 | 200 | 94 | 0 |
| 9 | 200 | 100 | 0 |
| 10 | 200 | 100 | 0 |
| 11 | 200 | 100 | 0 |
| 12 | 200 | 100 | 0 |
| 13 | 200 | 94 | 0 |
| 14 | 200 | 100 | 0 |
| 15 | 200 | 100 | 0 |
| 16 | 200 | 91 | 0 |

TABLE 3-continued

| Compound No. | Concentration of active ingredient (ppm) | Prevention value when inoculated with drug-resistant strain (%) | Prevention value when inoculated with drug-sensitive strain (%) |
| --- | --- | --- | --- |
| 17 | 200 | 88 | 0 |
| 18 | 200 | 100 | 0 |
| 19 | 200 | 94 | 0 |
| 20 | 200 | 95 | 0 |
| 21 | 200 | 100 | 0 |
| 22 | 200 | 100 | 0 |
| 23 | 200 | 97 | 0 |
| 24 | 200 | 94 | 0 |
| 25 | 200 | 100 | 0 |
| 26 | 200 | 88 | 0 |
| 27 | 200 | 94 | 0 |
| 28 | 200 | 100 | 0 |
| 29 | 200 | 97 | 0 |
| 30 | 200 | 100 | 0 |
| 31 | 200 | 91 | 0 |
| 32 | 200 | 88 | 0 |
| 33 | 200 | 88 | 0 |
| 34 | 200 | 81 | 0 |
| 35 | 200 | 100 | 0 |
| 36 | 200 | 100 | 0 |
| A | 200 | 0 | 100 |
| B | 200 | 0 | 100 |
| C | 200 | 0 | 100 |
| D | 200 | 0 | 100 |

EXPERIMENT 2

Fungitoxic activity against *Pseudocercosporella herpotrichoides*

Test compounds were each dissolved in dimethylsulfoxide to make desired concentrations, mixed with melted PDA (potato dextrose agar) and poured into petri dishes. Spore suspensions of *Pseudocercosporella herpotrichoides* were inoculated on the solidified plates, and incubation was performed at 23° C. for 7 days. The evaluation of the fungitoxic activity was made according to the degree of fungal growth on the following criteria:

—: no fungal growth was observed
±: slight fungal growth was observed
+: fungal growth less than that in the untreated plot was observed
++: fungal growth equal to that in the untreated plot was observed The results are shown in Table 4.

TABLE 4

| Compound No. | Concentration of active ingredient (ppm) | Fungitoxic activity when inoculated with drug-resistant strain | Fungitoxic activity when inoculated with drug-sensitive strain |
| --- | --- | --- | --- |
| 1 | 100 | — | — |
|  | 10 | — | ++ |
|  | 1 | — | ++ |
|  | 0.1 | — | ++ |
| 2 | 100 | — | ++ |
|  | 10 | — | ++ |
|  | 1 | — | ++ |
|  | 0.1 | + | ++ |
| 3 | 100 | — | — |
|  | 10 | — | ++ |
|  | 1 | — | ++ |
|  | 0.1 | — | ++ |
| 4 | 100 | — | ++ |
|  | 10 | — | ++ |
|  | 1 | — | ++ |
| 5 | 100 | — | ++ |
|  | 10 | — | ++ |
|  | 1 | — | ++ |
| 6 | 100 | — | ++ |
|  | 10 | — | ++ |
|  | 1 | — | ++ |
| 7 | 100 | — | ++ |
|  | 10 | — | ++ |
|  | 1 | — | ++ |
| 8 | 100 | — | ++ |
|  | 10 | — | ++ |
|  | 1 | ± | ++ |
| 9 | 100 | — | — |
|  | 10 | — | ± |
|  | 1 | — | ++ |
|  | 0.1 | — | ++ |
|  | 0.05 | — | ++ |
| 10 | 100 | — | + |
|  | 10 | — | ++ |
|  | 1 | — | ++ |
|  | 0.1 | — | ++ |
|  | 0.05 | — | ++ |
| 11 | 100 | — | + |
|  | 10 | — | ++ |
|  | 1 | — | ++ |
|  | 0.1 | — | ++ |
|  | 0.05 | — | ++ |
| 12 | 100 | — | — |
|  | 10 | — | ++ |
|  | 1 | — | ++ |
|  | 0.1 | — | ++ |
| 13 | 100 | — | ++ |
|  | 10 | — | ++ |
|  | 1 | — | ++ |
|  | 0.1 | — | ++ |
| 15 | 100 | — | ++ |
|  | 10 | — | ++ |
|  | 1 | ± | ++ |
| 16 | 100 | — | ++ |
|  | 10 | — | ++ |
|  | 1 | — | ++ |
|  | 0.1 | — | ++ |
| 17 | 100 | — | ++ |
|  | 10 | — | ++ |
|  | 1 | — | ++ |
|  | 0.1 | — | ++ |
| 18 | 100 | — | ++ |
|  | 10 | — | ++ |
|  | 1 | — | ++ |
|  | 0.1 | — | ++ |
| 19 | 100 | — | ++ |
|  | 10 | — | ++ |
|  | 1 | — | ++ |
| 21 | 100 | — | — |
|  | 10 | — | ++ |
|  | 1 | — | ++ |
| 22 | 100 | — | ++ |
|  | 10 | — | ++ |
|  | 1 | — | ++ |
|  | 0.1 | — | ++ |
| 23 | 100 | — | ++ |
|  | 10 | — | ++ |
|  | 1 | — | ++ |
|  | 0.1 | — | ++ |
| 24 | 100 | — | + |
|  | 10 | — | ++ |
|  | 1 | — | ++ |
| 25 | 100 | — | ++ |
|  | 10 | — | ++ |
|  | 1 | — | ++ |
| 26 | 100 | — | ++ |
|  | 10 | — | ++ |
|  | 1 | ± | ++ |
| 27 | 100 | — | ++ |
|  | 10 | — | ++ |
|  | 1 | ± | ++ |
| 28 | 100 | — | ++ |
|  | 10 | — | ++ |
|  | 1 | — | ++ |

TABLE 4-continued

| Compound No. | Concentration of active ingredient (ppm) | Fungitoxic activity when inoculated with drug-resistant strain | Fungitoxic activity when inoculated with drug-sensitive strain |
|---|---|---|---|
| 29 | 100 | − | ++ |
|  | 10 | − | ++ |
|  | 1 | − | ++ |
| 31 | 100 | − | ++ |
|  | 25 | − | ++ |
|  | 6.3 | − | ++ |
|  | 1.6 | − | ++ |
|  | 0.4 | − | ++ |
|  | 0.1 | ± | ++ |
| 32 | 100 | − | + |
|  | 25 | − | ++ |
|  | 6.3 | − | ++ |
|  | 1.6 | − | ++ |
|  | 0.4 | − | ++ |
|  | 0.1 | − | ++ |
| 33 | 100 | − | ++ |
|  | 25 | − | ++ |
|  | 6.3 | ± | ++ |
| 34 | 100 | − | ++ |
|  | 25 | − | ++ |
|  | 6.3 | − | ++ |
| 36 | 100 | − | + |
|  | 25 | − | + |
|  | 6.3 | − | + |
| A | 100 | + | ± |
|  | 10 | ++ | ± |
|  | 1 | ++ | ± |

EXPERIMENT 3

Preventive effect on gray mold of tomato (*Botrytis cinerea*)

A plastic pot of 90 ml volume was filled with sandy soil, and seeds of tomato (var: Fukuju No. 2) were sowed therein. Cultivation was carried out in a greenhouse for 4 weeks. Onto the resulting seedlings at the 4-leaf stage, the test compound(s) formulated in emulsifiable concentrate or wettable powder and diluted with water were sprayed at a rate of 30 ml per pot. Then, the seedlings were inoculated with a mixed spore suspension of the drug-resistant and drug-sensitive strain of *Botrytis cinerea* by spraying and placed at 20° C. in a room of high humidity for 5 days. The degree of damage was determined in the same manner as in Experiment 1, and the results are shown in Table 5.

TABLE 5

| Compound No. | Concentration of active ingredient (ppm) | Prevention value (%) |
|---|---|---|
| 1 | 100 | 32 |
| 1 | 20 | 0 |
| 2 | 100 | 34 |
| 2 | 20 | 0 |
| 3 | 100 | 30 |
| 3 | 20 | 0 |
| 4 | 100 | 28 |
| 4 | 20 | 0 |
| 9 | 100 | 36 |
| 9 | 20 | 0 |
| 10 | 100 | 30 |
| 10 | 20 | 0 |
| 13 | 100 | 28 |
| 13 | 20 | 0 |
| 14 | 100 | 34 |
| 14 | 20 | 0 |
| 21 | 100 | 38 |
| 21 | 20 | 0 |
| 24 | 100 | 32 |
| 24 | 20 | 0 |
| A | 100 | 46 |
| A | 20 | 18 |
| B | 100 | 50 |
| B | 20 | 24 |
| C | 100 | 48 |
| C | 20 | 22 |
| D | 100 | 44 |
| D | 20 | 16 |
| E | 100 | 48 |
| E | 20 | 20 |
| F | 500 | 44 |
| F | 100 | 16 |
| G | 100 | 40 |
| G | 20 | 18 |
| H | 500 | 42 |
| H | 100 | 10 |
| 1 + A | 10 + 20 | 100 |
| 1 + B | 10 + 20 | 100 |
| 1 + C | 10 + 20 | 100 |
| 1 + D | 10 + 20 | 100 |
| 2 + E | 10 + 20 | 100 |
| 2 + F | 10 + 20 | 100 |
| 2 + G | 10 + 20 | 100 |
| 2 + H | 10 + 20 | 100 |
| 3 + A | 10 + 20 | 100 |
| 4 + B | 10 + 20 | 100 |
| 9 + C | 10 + 20 | 100 |
| 10 + D | 10 + 20 | 100 |
| 13 + E | 10 + 20 | 100 |
| 14 + F | 10 + 20 | 100 |
| 21 + G | 10 + 20 | 100 |
| 24 + H | 10 + 20 | 100 |

What is claimed is:

1. A method for controlling plant pathogenic fungi which are resistant to benzimidazole or thiophanate fungicides which comprises applying a fungicidally effective amount of at least one compound of the formula:

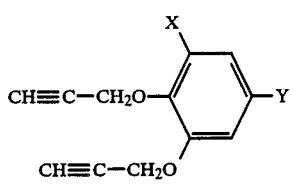

wherein X is a hydrogen atom, a halogen atom, a $C_1$-$C_3$ alkyl group or a $C_1$-$C_3$ alkoxy group and Y is a hydrogen atom, a halogen atom, an ethylene-dioxymethyl group, a hydroxyl group, a hydroxymethyl group or —$CH(OR^3)_2$ wherein $R^3$ is a $C_1$-$C_3$ alkyl group with the proviso that X and Y are not simultaneously hydrogen atoms, to plant pathogenic fungi which are resistant to benzimidazole or thiophanate fungicides.

2. A method for controlling plant pathogenic fungi which are resistant to benzimidazole or thiophanate fungicides which comprises applying a fungicidally effective amount of at least one compound of the formula:

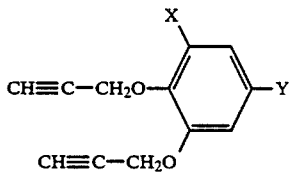

wherein X is a hydrogen atom, a halogen atom, a $C_1$-$C_3$ alkyl group or a $C_1$-$C_3$ alkoxy group and Y ia a hydrogen atom, a halogen atom, a cyano group, a formyl group, an ethylene dioxymethyl group, a hydroxy group, a hydroxy-methyl group, —CH=N—OR$^1$, or —CH(OR$^3$)$_2$;

wherein $R^1$ is a hydrogen atom, a $C_1$-$C_3$ alkyl group, a $C_3$-$C_5$ alkenyl group, a $C_3$-$C_5$ alkynyl group, a halo ($C_3$-$C_5$) alkynyl group or a phenyl substituted $C_1$-$C_3$ alkyl group, or a cyano substituted $C_1$-$C_3$ alkyl group; and $R^3$ is a $C_1$-$C_3$ alkyl group, with the proviso that X and Y are not simultaneously hydrogen, to plant pathogenic fungi which are resistant to benzimidazole or thiophanate fungicides.

* * * * *